(12) United States Patent
Volke et al.

(10) Patent No.: US 6,899,677 B1
(45) Date of Patent: May 31, 2005

(54) COUPLING MEDIUM FOR TRANSVERSAL ULTRASONIC WAVES

(75) Inventors: Frank Volke, St. Ingbert (DE); Jürgen Meiche, St. Ingbert (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 10/069,773

(22) PCT Filed: Aug. 22, 2000

(86) PCT No.: PCT/DE00/02887

§ 371 (c)(1),
(2), (4) Date: Jun. 5, 2002

(87) PCT Pub. No.: WO01/16590

PCT Pub. Date: Mar. 8, 2001

(30) Foreign Application Priority Data

Aug. 30, 1999 (DE) .......................... 199 41 198

(51) Int. Cl.$^7$ ................ A61B 8/00; G01N 29/28
(52) U.S. Cl. ................ 600/437; 73/644; 252/408.1; 516/105
(58) Field of Search ................ 516/105, 106, 516/107; 73/644; 128/660.01; 252/408.1; 600/437

(56) References Cited

U.S. PATENT DOCUMENTS

| | | | | |
|---|---|---|---|---|
| 3,427,382 A | * | 2/1969 | Haefele | 424/70.13 |
| 3,655,579 A | * | 4/1972 | Crotty et al. | 516/107 |
| 3,826,127 A | * | 7/1974 | Molina | 73/644 |
| 3,939,101 A | * | 2/1976 | Molina | 252/301.19 |
| 4,002,221 A | * | 1/1977 | Buchalter | 73/644 |
| 4,453,408 A | * | 6/1984 | Clayman | 73/1.86 |
| 4,905,700 A | | 3/1990 | Wokalek et al. | 128/660.01 |
| 5,579,769 A | * | 12/1996 | Yoshida et al. | 600/437 |
| 6,039,694 A | * | 3/2000 | Larson et al. | 73/644 |

FOREIGN PATENT DOCUMENTS

| | | |
|---|---|---|
| DE | 196 11 769 A | 9/1997 |
| EP | 0 211 482 A2 | 2/1987 |
| JP | 07-124154 A | 5/1995 |

OTHER PUBLICATIONS

On www, "Chemical Composition of Honey": http://www.chemsoc.org/exemplarchem/entries/2001/loveridge/index–page3.html, 3 pages, Aug. 2004.*
On www, "Definition of Honey and Honey Products": http://www.nhb.org/foodtech/defdoc.html, 5 pages, Aug. 2004.*
Hawley's Condensed Chemical Dictionary, Eleventh Edition, edited by Sax and Lewis, Sr. (Van Nostrand Reinhold Company, Ney York, NY, copyright 1987), Oct. 1989, p. 193.*
Encyclopedia of food Technology, Edited by Arnold H. Johnson, Ph.D. & Martin S. Peterson, Ph.D., (The AVI Publishing Co, Inc., Westport, Conn., 1974), pp. 1–3–108, (May 1975).*
Van Nostrand's Scientific Encyclopedia, Eight Edition, (Van Nostrand Reinhold, NY, NY), pp. 1607 (May 1999).*
Hawley's Condensed Chemical Dictionary, Eleventh Edition, edited by Sax and Lewis, Sr. (Van Nostrand Reinhold Company, Ney York, NY, copyright 1987), Oct. 1989, p. 943.*
The Merck Index An Encyclopedia of Chemicals, Drugs, and Biologicals, Tenth Edition, (Merck & Co, Inc. Rahway, NJ, 1983) p. 495 entry No. 3409, Jan. 17, 1984.*
Webster's II new Riverside university dictionary, (Riverside Publishing Co, A Houghton Mifflin Co., Boston, MA, copyright 1984) pp. 703, 913, 1228, 1984—month unknown.*
J. Krautkruml åmer, Werkstoffprüfung mit Ultraschall, 5$^{th}$ Ed., 1986, Springer, p. 297, (with partial translation), 1986, month unknown.
J. Krautkrämer et al., "Werkstoffprüfung mit Ultraschall", 5$^{th}$ ed. 1986, Springer, p. 296–299, 1986, month unknown.

* cited by examiner

*Primary Examiner*—Daniel S. Metzmaier
(74) *Attorney, Agent, or Firm*—Venable LLP; Robert Kinberg; Marina V. Schneller

(57) ABSTRACT

A coupling medium of a thin layer of a homogenized mixture of at least one polysaccharide or disaccharide such as trehalose; a surface-active substance such as sodium dioctylsulfosuccinate; and water acts as a coupling medium for transverse ultrasonic waves, when the homogenized mixture is applied to surfaces of a transmitting, respectively receiving, transducer for transverse ultrasonic waves; and a surface of a probe.

3 Claims, No Drawings

COUPLING MEDIUM FOR TRANSVERSAL ULTRASONIC WAVES

The present invention relates to a novel coupling agent for transverse ultrasonic waves, such as are, for example, employed in the field of material testing.

The use of transverse ultrasonic waves in non-destructive material testing occurs by means of respective transverse ultrasonic wave transducers mounted on the surface of the test piece. Measuring may occur using a pulse-echo method or a transmission process. The elastic constants of the test piece material, for example, can be measured from the transit times of the ultrasonic pulses.

Coupling of transverse ultrasonic waves into the test piece requires a corresponding coupling agent between the transmitting respectively the receiving transducer and the surface of the test piece. Although numerous coupling agents for coupling in longitudinal sound waves are known in the art, for example, providing corresponding materials for coupling in transverse sound waves presents major problems. Such coupling agents must possess sufficient shear stability therefore, for example, water is unsuitable.

J. Krautkrämer et al.: "Werkstoffprüfung mit Ultraschall", 5th ed. 1986, Springer, page 297, mentions, in particular, viscous materials, such as cable impregnation media, super-heated cylinder oil or gear lubricant oil (SAE 90), as suited coupling agents. Furthermore, reference is made to adhesive wax, low-melting point salts and plastic adhesives with which the probe can be permanently glued onto the surface of the test piece.

However, all these materials do not possess satisfactory properties and frequently cannot be reproducibly provided. In particular, employing gear lubricant oil is, according to own tests, only successful in the lower ultrasonic frequency range (<1 MHz). In higher frequency ranges between 1 and 20 MHz such as are utilized in material testing, the oil is not suited for coupling in transverse ultrasonic sound waves.

Permanent coupling by gluing the probe onto the test piece is not recommendable solely on the basis of useable testing velocities.

Another substance known in the art as a coupling agent for transverse ultrasonic waves is honey. However, honey as well as glue cannot be reproducibly produced, are unpleasantly sticky and cannot be easily completely removed from the surface of the test piece. Moreover, commercially available media for coupling in transverse ultrasonic waves produced on a honey basis and whose appearance has been altered by colorants are expensive.

An essential property that a coupling medium for transverse ultrasonic waves should possess is that it be reproducibly producible and the ability to be able to generate a very thin layer of this medium between the probe and the surface of the test piece. The reason therefor is the principle of transit time measurement. The overall transit time of the sound between the transmitting transducer and the receiving transducer is composed of the portions of the transit time of the sound in the individual components of the system, i.e. in the case of transmission measurement of the transit time in the coupling layer between the transmitting transducer and the test piece, the transit time in the test piece and the transit time in the coupling layer between the test piece and the receiving transducer. Therefore, for accurate measurement it is necessary to either know the thickness of the coupling media and the sound velocities occurring therein exactly or to generate an extremely thin, only a few atom layers thick coupling layer, whose transit time portion is negligible for measurement precision.

These requirements in particular present problems in the state-of-the-art coupling agents. On the one hand, their sound velocity is not always known, on the other hand they cannot be generated with a defined thickness between the surface of the probe and the test piece, which, for example, is only dependent on the pressure force of the transducer on the probe. The frequently employed honey-based coupling medium forms crystals when pressed so that the thickness of this coupling layer differs from measurement to measurement, thus is undefinable. Crystal formation depends on non-controllable peripheral conditions such as temperature, humidity, water content, etc. Moreover, coupling media for longitudinal ultrasonic waves, such as in particular used in medical diagnosis are known from the state of the art. U.S. Pat. No. 4,905,700 describes an ultrasonic coupling medium, which comprises a hydrogel foil, with a water content of >90% and polysaccharide, for examining the human body.

Furthermore, JP 07/124154 discloses a contact medium, comprising a gel composed of polysaccharides, for ultrasonic applications in medical diagnosis. The water content of the gel lies above 80%. In this case, too, the field of application being medical diagnosis, the coupling medium is for longitudinal ultrasonic waves, but not a coupling medium for transverse ultrasonic waves.

The demands on a coupling medium for transverse ultrasonic waves distinctly differ from the demands on a coupling medium for longitudinal waves so that the coupling media mentioned in the cited printed publications are completely unsuited for coupling transverse ultrasonic waves.

On the basis of these problems of the state of the art, the object of the present invention is to provide a coupling medium for transverse ultrasonic waves that possesses good coupling properties for transverse ultrasonic waves, is reproducible and its thickness between the surfaces of the probe and the test piece can be reproducibly set. This object is solved with the medium of claims 1 respectively 3. Advantageous embodiments are described in the subclaims.

A key element of the invention is that is was recognized that a homogeneous mixture of a polysaccharide, a surface-active substance and water is excellently suited as a coupling medium for transverse ultrasonic waves, with polysaccharides also including disaccharides. Such a medium can be easily produced,in a reproducible manner and possesses excellent coupling properties. The coupling medium of this composition is white and creamy, thus has a pleasant consistency and appearance. This medium can be colored as desired and is durable. Moreover, it can be easily removed from the surface of the test piece with water.

With the invented coupling medium, transverse ultrasonic waves can be coupled into materials of different composition, for example skin, surfaces of solids, test pieces, etc. The coupling medium reacts excellently to shear forces and coupling performance is comparable to the previously used but not standardized coupling media such as glue and honey. Furthermore, it is a very economical variant of a coupling medium.

In a preferred embodiment, solely non-toxic and biocompatible polysaccharides and surface-active substances are employed.

The invented coupling medium has the particular advantage that its thickness can be reproducibly set following application to the surface of the test piece or the probe. This thickness can be generated by a defined pressure force of the probe onto the surface of the test piece. Applying the same pressure in each measurement yields the same layer thickness of the coupling medium. Moreover, with the coupling medium, very thin layers of only a few atom layers can be generated between the surfaces of the probe and the test piece so that the transit time of the ultrasonic wave in this coupling layer is negligible.

A special feature of the present invention is the reproducible, low acoustic attenuation of the developed coupling medium, with the transmitted portion of the sound waves increasing in comparison to the agents known in the state of the art.

This is achieved by means of the settable, infinitesimal thickness of the coupling layer and by means of the low attenuation coefficients of the material. In this manner, with given excitation energy, higher intensity is at disposal inside the probe so that deeper lying structure become detectable at all or better.

The mixture ratios of water, surface-active substance and polysaccharide lie preferably in the range from 10 to 30 weight percent for water, from 10 to 30 weight percent for the surface-active substance and from 4.0 to 80 weight percent for the polysaccharide.

Preferably the polysaccharides are, starch, hyaluron acid, polyglucane, amylose, dextrin, and disaccharides such as sucrose, saccharose and trehalose. Lipids, Aerosol-OT®, phospholipids and glycolipids are preferably employed as surface-active substances.

The especially good transmission of the shear forces is particularly yielded by the three-dimensionally linked molecular structure which forms in the invented mixture and immobilizes the water sufficiently molecularly in the microspaces.

In the following, a preferred embodiment of such a coupling medium is described. A mixture of Aerosol-OT® with a weight percent of 22, trehalose with a weight percent of 56 and water with a weight percent of 22 is produced in the following steps:

1. Production of an Aerosol-OT® dispersion with little water creating a high-viscous dispersion.

2. Stepwise addition of trehalose and water while stirring until a homogeneous mixture is yielded.

What is claimed is:

1. A method of transmitting transverse ultrasonic waves between a surface of a transmitting, respectively receiving, transducer for transverse ultrasonic waves; and a surface of a probe, wherein said method comprises providing a homogenized mixture of at least one polysaccharide or one disaccharide, a surface-active substance and water as a coupling medium for transverse ultrasonic waves and applying said homogenized mixture to at least one of either said surface of a transmitting, respectively receiving, transducer for transverse ultrasonic waves or a surface of a probe; and pressing said probe and said transducer together, wherein said mixture comprises 10 to 30 weight % water, 10 to 30 weight % of surface active substance and 40 to 80 weight % of polysaccharide or disaccharide.

2. The method of claim 1, wherein said mixture is composed solely of biocompatible substances.

3. The method of claim 1, wherein the surface active substance is selected from the group consisting of lipids, aerosol-OT, phospholipids, and glycolipids.

* * * * *